US00PP14716P2

(12) United States Plant Patent
Drewlow

(10) Patent No.: US PP14,716 P2
(45) Date of Patent: Apr. 20, 2004

(54) KALANCHOE PLANT NAMED 'FOREVER MIDI ORANGE GLOW'

(50) Latin Name: *Kalanchoe blossfeldiana*
Varietal Denomination: Forever Midi Orange Glow

(75) Inventor: Lyndon W. Drewlow, Lompoc, CA (US)

(73) Assignee: Oglevee Ltd., Connellsville, PA (US)

( * ) Notice: Subject to any disclaimer, the term of this patent is extended or adjusted under 35 U.S.C. 154(b) by 0 days.

(21) Appl. No.: 10/377,503

(22) Filed: Feb. 28, 2003

(51) Int. Cl.[7] ..... A01H 5/00
(52) U.S. Cl. ..... Plt./340
(58) Field of Search ..... Plt./340

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Kalanchoe plant named 'Forever Midi Orange Glow', characterized by its compact, upright, dense and uniform plant habit; freely branching growth habit; numerous large orange red-colored flowers; small dark green-colored leaves; and excellent postproduction longevity.

1 Drawing Sheet

Botanical classification/cultivar designation: *Kalanchoe blossfeldiana* cultivar Forever Midi Orange Glow.

BACKGROUND OF THE INVENTION

The present invention relates to a new and distinct cultivar of Kalanchoe plant, botanically known as *Kalanchoe blossfeldiana,* and hereinafter referred to by the cultivar name 'Forever Midi Orange Glow'.

The new Kalanchoe is a product of a planned breeding program conducted by the Inventor in Ashtabula, Ohio. The objective of the breeding program was to create new compact, freely-branching and freely-flowering Kalanchoe cultivars with attractive leaf and flower coloration.

The new Kalanchoe originated from a cross-pollination made by the Inventor in November, 1998 of a proprietary selection of *Kalanchoe blossfeldiana* identified as code number 98-300-3, not patented, as the female, or seed, parent with a proprietary selection of *Kalanchoe blossfeldiana* identified as code number 97-226-9, not patented, as the male, or pollen, parent. The cultivar Forever Midi Orange Glow was discovered and selected by the Inventor as a flowering plant within the progeny of the stated cross-pollination in a controlled environment in Ashtabula, Ohio.

Asexual reproduction of the new Kalanchoe by terminal vegetative cuttings taken at Lompoc, Calif., since December, 1999, has shown that the unique features of this new Kalanchoe are stable and reproduced true to type in successive generations.

BRIEF SUMMARY OF THE INVENTION

The cultivar Forever Midi Orange Glow has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Forever Midi Orange Glow'. These characteristics in combination distinguish 'Forever Midi Orange Glow' as new and distinct cultivar:

1. Compact, upright, uniform and dense plant habit.
2. Freely branching growth habit.
3. Numerous large orange red-colored flowers.
4. Small dark green-colored leaves.
5. Excellent postproduction longevity.

Plants of the new Kalanchoe differ from plants of the parent selections primarily in plant habit and flower color.

Plants of the new Kalanchoe can be compared to plants of the cultivar Forever Midi Orange Ember. In side-by-side comparisons conducted by the Inventor in Lompoc, Calif., plants of the new Kalanchoe differed from plants of the cultivar Forever Midi Orange Ember in the following characteristics:

1. Plants of the new Kalanchoe were more compact and more mounded than plants of the cultivar Forever Midi Orange Ember.
2. Plants of the new Kalanchoe had smaller leaves than plants of the cultivar Forever Midi Orange Ember.
3. Plants of the new Kalanchoe had larger flowers than plants of the cultivar Forever Midi Orange Ember.
4. Plants of the new Kalanchoe flowered about three to four days earlier than plants of the cultivar Forever Midi Orange Ember.
5. Flower color of plants of the new Kalanchoe was slightly lighter than flower color of plants of the cultivar Forever Midi Orange Ember.

BRIEF DESCRIPTION OF THE PHOTOGRAPH

The accompanying colored photograph illustrates the overall appearance of the new Kalanchoe, showing the colors as true as it is reasonably possible to obtain in colored reproductions of this type. Colors in the photograph may differ slightly from the color values cited in the detailed botanical description which accurately describe the colors of the new Kalanchoe. The photograph comprises a side perspective view of a typical potted plant of 'Forever Midi Orange Glow'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photograph and for the description were grown during the winter in Lompoc, Calif., in a fiberglass-covered greenhouse. During the production of the plants, day temperatures ranged from 20 to 22° C.; night temperatures ranged from 16 to 18° C.; and light levels ranged from 3,000 to 4,000 footcandles. Rooted cuttings were planted in 10-cm containers and received long day/short night conditions (more than 14 hours of light) for about one week; plants then received natural short day/long night conditions (minimum 14 hours darkness) until flowering. Plants were about 12 weeks from the start of the short day/long night treatment when the photograph and the description were taken.

Botanical classification: *Kalanchoe blossfeldiana* cultivar Forever Midi Orange Glow.

Parentage:

*Female or seed parent.*—Proprietary selection of *Kalanchoe blossfeldiana* identified as code number 98-300-3, not patented.

*Male, or pollen, parent.*—Proprietary selection of *Kalanchoe blossfeldiana* identified as code number 97-226-9, not patented.

Propagation:

*Type cutting.*—Terminal vegetative cuttings.

*Time to initiate roots.*—Summer: About 10 days at 21° C. Winter: About 12 days at 21° C.

*Time to produce a rooted cutting.*—Summer: About 21 days at 21° C. Winter: About 23 days at 21° C.

*Root description.*—Fine, fibrous, freely branching, and grayed white in color.

Plant description:

*Form.*—Compact, upright, uniform and dense plant habit. Freely flowering with numerous compound cymes. Inverted triangle; mounded crown. Appropriate for 10-cm containers; vigorous growth habit.

*Plant height at flowering.*—About 12 cm.

*Plant diameter at flowering.*—About 18 to 20 cm.

*Branching habit.*—Freely branching habit; typically eight to ten lateral branches develop per plant. Pinching (removal of terminal apex) is not required but will enhance lateral branch development.

*Lateral branch description.*—Length: About 8 to 10 cm. Diameter: About 3 to 4 cm. Internode length: About 8 to 10 mm. Aspect: About 35 to 40° from vertical. Strength: Strong. Texture: Smooth, glabrous. Color: 146D.

*Foliage description.*—Arrangement: Opposite, simple. Length: About 5 to 6 cm. Width: About 4 to 4.5 cm. Shape: Ovate. Apex: Acute to obtuse. Base: Rounded. Margin: Crenate, shallow lobed. Texture, upper and lower surfaces: Coriaceous, glabrous and succulent. Venation pattern: Pinnate. Color: Developing leaves, upper surface: 146A. Developing leaves, lower surface: 146B. Fully expanded leaves, upper surface: 147A; under high light levels and cool production temperatures margins may be tinged with 185B. Fully expanded leaves, lower surface: 147B. Venation, upper surface: 147A. Venation, lower surface: 147B. Petiole length: About 1 to 1.2 cm. Petiole diameter: About 5 mm. Petiole texture: Smooth, glabrous. Petiole color, upper surface: 147B, tinged with 185B. Petiole color, lower surface: 147B.

Flower description:

*Flower type and habit.*—Single flowers arranged in axillary compound dichasial cymes. Freely flowering; more than 30 flowers per lateral branch and more than 200 flowers per plant. Flowers not persistent. Flowers not fragrant. Flowers face mostly upright.

*Natural flowering season.*—Plants of the new Kalanchoe initiate and develop flowers under short day/long night conditions or during the late autumn/winter/early spring. Flower initiation and development can also be induced under artificial short day/long night conditions (at least 14 hours of darkness).

*Time to flower.*—Under short day/long night photoinductive conditions, about 9 to 9.5 weeks are required. Actual time to flower is primarily dependent upon temperature and light intensity.

*Post-production longevity.*—Excellent post-production longevity; plants maintain good foliage and flower substance for at least four weeks under interior environmental conditions. Individual flowers last about two weeks on the plant.

*Flower diameter.*—About 1.8 cm.

*Flower height.*—1.2 cm.

*Flower buds.*—Shape: Oblong. Length: About 1.2 cm. Width: About 4 mm. Color: 145A, towards apex, 40A.

*Petals.*—Quantity: Four fused at base. Length: About 9 mm. Width: About 6 mm. Shape: Ovate to rounded. Apex: Cuspidate. Margin: Entire. Texture, upper and lower surfaces: Glabrous, smooth, satiny. Color: When opening, upper surface: 40A. When opening, lower surface: 33D. Fully opened, upper surface: 33A; color does not fade with development. Fully opened, lower surface: 33C with random areas 33B; color does not fade with development.

*Sepals.*—Quantity: Four fused at base. Length: About 7 mm. Width: About 2 mm. Shape: Lanceolate. Apex: Acuminate. Base: Rounded. Margin: Entire. Texture, upper and lower surfaces: Glabrous, smooth. Color: Immature, upper surface: 146D. Immature, lower surface: 145C. Mature, upper surface: 145C. Mature, lower surface: 145D.

*Peduncle.*—Length: About 2 cm. Diameter: About 2 mm. Angle: About 45° from vertical. Strength: Strong, flexible. Texture: Smooth, glabrous. Color: 146C.

*Pedicels.*—Length: About 2 mm. Diameter: About 1 mm. Angle: About 45° from vertical. Strength: Strong, flexible. Texture: Smooth, glabrous. Color: 146C.

*Reproductive organs.*—Stamens: Quantity per flower: Eight. Anther shape: Elliptic; flat. Anther size: Less than 1 mm. Anther color: Yellowish green. Pollen amount: Abundant. Pollen color: Close to 12A. Pistils: Quantity per flower: Four. Style length: About 3 mm. Style color: Light yellow green. Stigma shape: Flat, rounded. Stigma color: Close to 155D. Ovary color: 146C.

*Seed.*—Length: Less than 1 mm. Diameter: Less than 1 mm. Color: Close to 166C.

Disease/pest resistance: Plants of the new Kalanchoe have not been observed to be resistant to pathogens and pests common to Kalanchoes.

Temperature tolerance: Plants of the new Kalanchoe have been observed to tolerate low temperatures of 10° C. and high temperatures of 35° C.

It is claimed:

1. A new and distinct cultivar of Kalanchoe plant named 'Forever Midi Orange Glow', as illustrated and described.

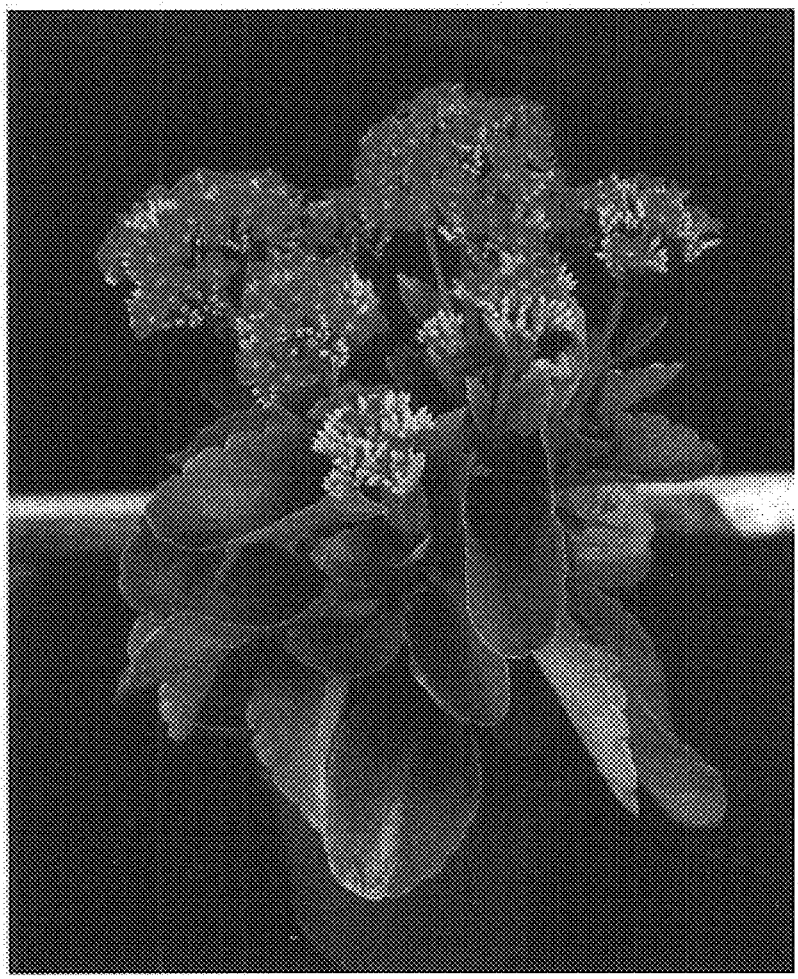

* * * * *